United States Patent
Baril et al.

(10) Patent No.: US 11,399,888 B2
(45) Date of Patent: Aug. 2, 2022

(54) BIPOLAR PENCIL

(71) Applicant: COVIDIEN LP, Mansfield, MA (US)

(72) Inventors: Jacob C. Baril, Norwalk, CT (US); Matthew A. Dinino, Newington, CT (US); Roy J. Pilletere, North Haven, CT (US); Justin J. Thomas, New Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 379 days.

(21) Appl. No.: 16/540,593

(22) Filed: Aug. 14, 2019

(65) Prior Publication Data

US 2021/0045799 A1    Feb. 18, 2021

(51) Int. Cl.
*A61B 18/14*   (2006.01)
*A61B 18/16*   (2006.01)
*A61B 18/00*   (2006.01)

(52) U.S. Cl.
CPC ............ *A61B 18/148* (2013.01); *A61B 18/16* (2013.01); *A61B 2018/00083* (2013.01); *A61B 2018/00101* (2013.01); *A61B 2018/00601* (2013.01); *A61B 2018/1412* (2013.01); *A61B 2018/162* (2013.01); *A61B 2018/165* (2013.01)

(58) Field of Classification Search
CPC ... A61B 18/14; A61B 18/1404; A61B 18/148; A61B 18/16; A61B 2018/00083; A61B 2018/00101; A61B 2018/00178; A61B 2018/00601; A61B 2018/00916; A61B 2018/00922; A61B 2018/1412; A61B 2018/162; A61B 2018/165

USPC .................................................... 606/27–50
See application file for complete search history.

(56) References Cited

U.S. PATENT DOCUMENTS

| | | |
|---|---|---|
| 3,460,539 A | 8/1969 | Anhalt, Sr. |
| 3,768,482 A | 10/1973 | Shaw |
| 3,825,004 A | 7/1974 | Durden, III |
| 3,875,945 A | 4/1975 | Friedman |
| 3,987,795 A | 10/1976 | Morrison |
| 4,014,343 A * | 3/1977 | Esty .................. A61B 18/1402 606/45 |
| 4,161,950 A | 7/1979 | Doss et al. |
| 4,196,734 A | 4/1980 | Harris |
| 4,198,957 A | 4/1980 | Cage et al. |
| 4,228,800 A | 10/1980 | Degler, Jr. et al. |

(Continued)

*Primary Examiner* — Khadijeh A Vahdat
(74) *Attorney, Agent, or Firm* — Carter, DeLuca & Farrell LLP (57) ABSTRACT

An electrode assembly for an electrosurgical instrument includes a housing configured to operably receive a distal end of an instrument shaft, the housing including a pair of opposing spring clips. An active electrode is included having a proximal end configured to engage the distal end of the shaft and includes a cutting edge defined about a periphery thereof. An insulator is included that encapsulates the active electrode while leaving the cutting edge exposed. A pair of return electrodes is included that is each configured to operably engage an exposed side of the insulator, each return electrode including a recess defined therein configured to removably receive a distal end of each respective spring clip such that, upon selective engagement of the active electrode with the distal end of the shaft, each spring clip removably snaps into each respective recess to removably lock the active and return electrodes to the housing.

20 Claims, 8 Drawing Sheets

(56) References Cited

U.S. PATENT DOCUMENTS

| | | |
|---|---|---|
| 4,232,676 A | 11/1980 | Herczog |
| 4,443,935 A | 4/1984 | Zamba et al. |
| 4,485,810 A | 12/1984 | Beard |
| 4,545,375 A | 10/1985 | Cline |
| 4,549,073 A | 10/1985 | Tamura et al. |
| 4,562,838 A | 1/1986 | Walker |
| 4,589,411 A | 5/1986 | Friedman |
| 4,593,691 A | 6/1986 | Lindstrom et al. |
| 4,619,258 A | 10/1986 | Pool |
| 4,622,966 A | 11/1986 | Beard |
| 4,625,723 A | 12/1986 | Altnether et al. |
| 4,640,279 A | 2/1987 | Beard |
| 4,754,754 A | 7/1988 | Garito et al. |
| 4,785,807 A | 11/1988 | Blanch |
| 4,811,733 A | 3/1989 | Borsanyi et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,876,110 A | 10/1989 | Blanch |
| 4,909,249 A | 3/1990 | Akkas et al. |
| 4,911,159 A | 3/1990 | Johnson et al. |
| 5,013,312 A | 5/1991 | Parins et al. |
| 5,035,695 A | 7/1991 | Weber, Jr. et al. |
| 5,071,418 A | 12/1991 | Rosenbaum |
| 5,098,430 A | 3/1992 | Fleenor |
| 5,197,962 A | 3/1993 | Sansom et al. |
| 5,234,428 A | 8/1993 | Kaufman |
| 5,234,429 A | 8/1993 | Goldhaber |
| 5,254,082 A | 10/1993 | Takase |
| 5,262,241 A | 11/1993 | Huggins |
| 5,269,781 A | 12/1993 | Hewell, III |
| 5,300,087 A | 4/1994 | Knoepfler |
| 5,312,329 A | 5/1994 | Beaty et al. |
| 5,318,565 A | 6/1994 | Kuriloff et al. |
| 5,324,288 A | 6/1994 | Billings et al. |
| 5,330,470 A | 7/1994 | Hagen |
| 5,360,428 A | 11/1994 | Hutchinson, Jr. |
| 5,376,089 A | 12/1994 | Smith |
| 5,380,320 A | 1/1995 | Morris |
| 5,401,273 A | 3/1995 | Shippert |
| 5,413,575 A | 5/1995 | Haenggi |
| 5,437,665 A | 8/1995 | Munro |
| 5,441,499 A | 8/1995 | Fritzsch |
| 5,472,442 A | 12/1995 | Klicek |
| 5,484,434 A | 1/1996 | Cartmell et al. |
| 5,573,535 A | 11/1996 | Viklund |
| 5,609,573 A | 3/1997 | Sandock |
| 5,630,812 A | 5/1997 | Ellman et al. |
| 5,702,387 A | 12/1997 | Arts et al. |
| 5,720,745 A | 2/1998 | Farin et al. |
| 5,797,907 A | 8/1998 | Clement |
| 5,800,431 A | 9/1998 | Brown |
| 5,876,400 A | 3/1999 | Songer |
| 5,893,849 A | 4/1999 | Weaver |
| 5,951,548 A | 9/1999 | DeSisto et al. |
| 5,951,581 A | 9/1999 | Saadat et al. |
| 5,954,686 A | 9/1999 | Garito et al. |
| 5,989,248 A | 11/1999 | Tu et al. |
| 6,010,499 A | 1/2000 | Cobb |
| 6,059,782 A | 5/2000 | Novak et al. |
| 6,099,525 A | 8/2000 | Cosmescu |
| 6,355,034 B2 | 3/2002 | Cosmescu |
| 6,361,532 B1 | 3/2002 | Burek |
| 6,409,725 B1 | 6/2002 | Khandkar et al. |
| 6,511,479 B2 | 1/2003 | Gentelia et al. |
| 6,526,320 B2 | 2/2003 | Mitchell |
| 6,551,313 B1 | 4/2003 | Levin |
| 6,610,057 B1 | 8/2003 | Ellman et al. |
| 6,840,948 B2 | 1/2005 | Albrecht et al. |
| 6,855,140 B2 | 2/2005 | Albrecht et al. |
| 6,905,496 B1 | 6/2005 | Ellman et al. |
| 7,033,354 B2 | 4/2006 | Keppel |
| 7,112,199 B2 | 9/2006 | Cosmescu |
| 7,156,842 B2 | 1/2007 | Sartor et al. |
| 7,156,844 B2 | 1/2007 | Reschke et al. |
| 7,244,257 B2 | 7/2007 | Podhajsky et al. |
| 7,491,202 B2 | 2/2009 | Odom et al. |
| 7,503,917 B2 | 3/2009 | Sartor et al. |
| 7,563,261 B2 | 7/2009 | Carmel et al. |
| 7,736,361 B2 | 6/2010 | Palanker et al. |
| 7,846,158 B2 | 12/2010 | Podhajsky |
| 7,879,033 B2 | 2/2011 | Sartor et al. |
| 8,216,234 B2 | 7/2012 | Long |
| 8,235,987 B2 | 8/2012 | Craig |
| 8,251,996 B2 | 8/2012 | Hushka et al. |
| 8,597,292 B2 | 12/2013 | Kerr |
| 8,632,536 B2 | 1/2014 | Kerr et al. |
| 8,636,733 B2 | 1/2014 | Heard |
| 8,668,688 B2 | 3/2014 | Rusin |
| 8,882,766 B2 | 11/2014 | Couture et al. |
| 8,882,767 B2 | 11/2014 | Greep et al. |
| 8,968,301 B2 | 3/2015 | Weber |
| 8,998,899 B2 | 4/2015 | Shilev et al. |
| 9,060,765 B2 | 6/2015 | Rencher et al. |
| 9,144,453 B2 | 9/2015 | Rencher et al. |
| 9,498,275 B2 | 11/2016 | Wham et al. |
| 9,579,146 B2 | 2/2017 | Johnson et al. |
| 10,045,761 B2 | 8/2018 | Weber |
| 10,433,898 B2 | 10/2019 | Borgmeier et al. |
| 10,433,899 B2 | 10/2019 | Borgmeier et al. |
| 2001/0020167 A1* | 9/2001 | Woloszko .......... A61B 18/1492 606/45 |
| 2002/0103485 A1 | 8/2002 | Melnyk et al. |
| 2002/0111622 A1 | 8/2002 | Khandkar et al. |
| 2003/0088247 A1 | 5/2003 | Ineson |
| 2003/0212393 A1 | 11/2003 | Knowlton et al. |
| 2004/0030330 A1 | 2/2004 | Brassell et al. |
| 2004/0054370 A1 | 3/2004 | Given |
| 2005/0113824 A1 | 5/2005 | Sartor et al. |
| 2006/0041257 A1 | 2/2006 | Sartor et al. |
| 2006/0058783 A1 | 3/2006 | Buchman |
| 2006/0178667 A1 | 8/2006 | Sartor et al. |
| 2007/0181043 A1 | 8/2007 | Heim et al. |
| 2007/0260238 A1 | 11/2007 | Guerra |
| 2008/0281323 A1 | 11/2008 | Burbank et al. |

* cited by examiner

BIPOLAR PENCIL

BACKGROUND

Technical Field

The present disclosure relates generally to electrosurgical instruments and, more particularly, to an electrosurgical bipolar pencil configured for bipolar resection.

Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical coagulation, electrosurgical sealing, electrosurgical cutting, and/or electrosurgical fulguration or, in some instances, an electrosurgical blend thereof.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a handswitch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow preset control parameters and stay within known modes and power settings and electrosurgical pencils include simple and ergonomically friendly controls that are easily selected to regulate the various modes and power settings Electrosurgical instruments are typically configured such that power output can be adjusted without the surgeon having to turn his or her vision away from the operating site and toward the electrosurgical generator.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is an electrode assembly for an electrosurgical instrument that includes a housing configured to operably receive a distal end of an electrosurgical instrument shaft, the housing including a pair of opposing spring clips on either side thereof. An active electrode is included having a proximal end configured to selectively engage the distal end of the shaft, the active electrode including a cutting edge defined about a periphery thereof. An insulator is configured to encapsulate the active electrode while leaving the cutting edge exposed. A pair of return electrodes is included that is each configured to operably engage an exposed side of the insulator on opposing sides thereof, each return electrode including a recess defined therein configured to removably receive a distal end of each respective spring clip of the housing such that, upon selective engagement of the active electrode with the distal end of the shaft, each spring clip removably snaps into each respective recess to removably lock the active and return electrodes to the housing.

In aspects according to the present disclosure, the insulator is at least one of an electrical or thermal insulator. In other aspects according to the present disclosure, the active electrode includes tungsten. In still other aspects according to the present disclosure, the cutting edge of the active electrode is sharp to facilitate mechanical cutting of tissue.

In aspects according to the present disclosure, wherein the housing includes at least one detent configured to engage a corresponding at least one aperture defined within at least one of the spring clips. In other aspects according to the present disclosure, the housing includes two opposing housing halves configured to encapsulate the distal end of the shaft.

In aspects according to the present disclosure, a proximal end of the active electrode is configured to mechanically engage a collet defined within the distal end of the shaft. In other aspects according to the present disclosure, each spring clip includes a C-shaped distal end configured to abuttingly engage a proximal lip of each corresponding recess of each return electrode to removably retain each return electrode with the housing.

In aspects according to the present disclosure, the active electrode is generally arrow-shaped and includes a tip at an end thereof.

Provided in accordance with another aspects of the present disclosure is an electrode assembly for an electrosurgical instrument that includes a housing configured to operably receive a distal end of an electrosurgical instrument shaft, the housing including a pair of opposing housing halves configured to encapsulate the distal end of the shaft. A pair of opposing spring clips is disposed on respective housing halves. An active electrode is included having a proximal end configured to selectively engage the distal end of the shaft, the active electrode including a cutting edge defined about a periphery thereof. An insulator is configured to encapsulate the active electrode while leaving the cutting edge exposed. A pair of return electrodes is included that is each configured to operably engage an exposed side of the insulator on opposing sides thereof, each return electrode including a recess defined therein configured to removably receive a distal end of each respective spring clip of each housing half such that, upon selective engagement of the active electrode with the distal end of the shaft, a distal end of each spring clip removably snaps into each respective recess to removably lock the active and return electrodes to the housing.

In aspects according to the present disclosure, the insulator is at least one of an electrical or thermal insulator. In other aspects according to the present disclosure, the active electrode includes tungsten. In still other aspects according to the present disclosure, the cutting edge of the active electrode is sharp to facilitate mechanical cutting of tissue.

In aspects according to the present disclosure, the housing includes at least one detent configured to engage a corresponding at least one aperture defined within at least one of the spring clips. In other aspects according to the present disclosure, a proximal end of the active electrode is configured to mechanically engage a collet defined within the distal end of the shaft. In still other aspects according to the present disclosure, each spring clip includes a C-shaped distal end configured to abuttingly engage a proximal lip of each corresponding recess of each return electrode to removably retain each return electrode with the housing.

In aspects according to the present disclosure, the active electrode is generally arrow-shaped and includes a tip at an end thereof.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Particular embodiments of the presently disclosed electrosurgical pencil configured for bipolar resection are described in detail with reference to the drawing figures wherein like reference numerals identify similar or identical elements. As used herein, the term "distal" refers to that portion which is further from the user while the term "proximal" refers to that portion which is closer to the user or clinician. The term "leading edge" refers to the most forward edge with respect to the direction of travel while the term "trailing edge" refers to the edge opposite the leading edge with respect to the direction of travel.

Figure 1:
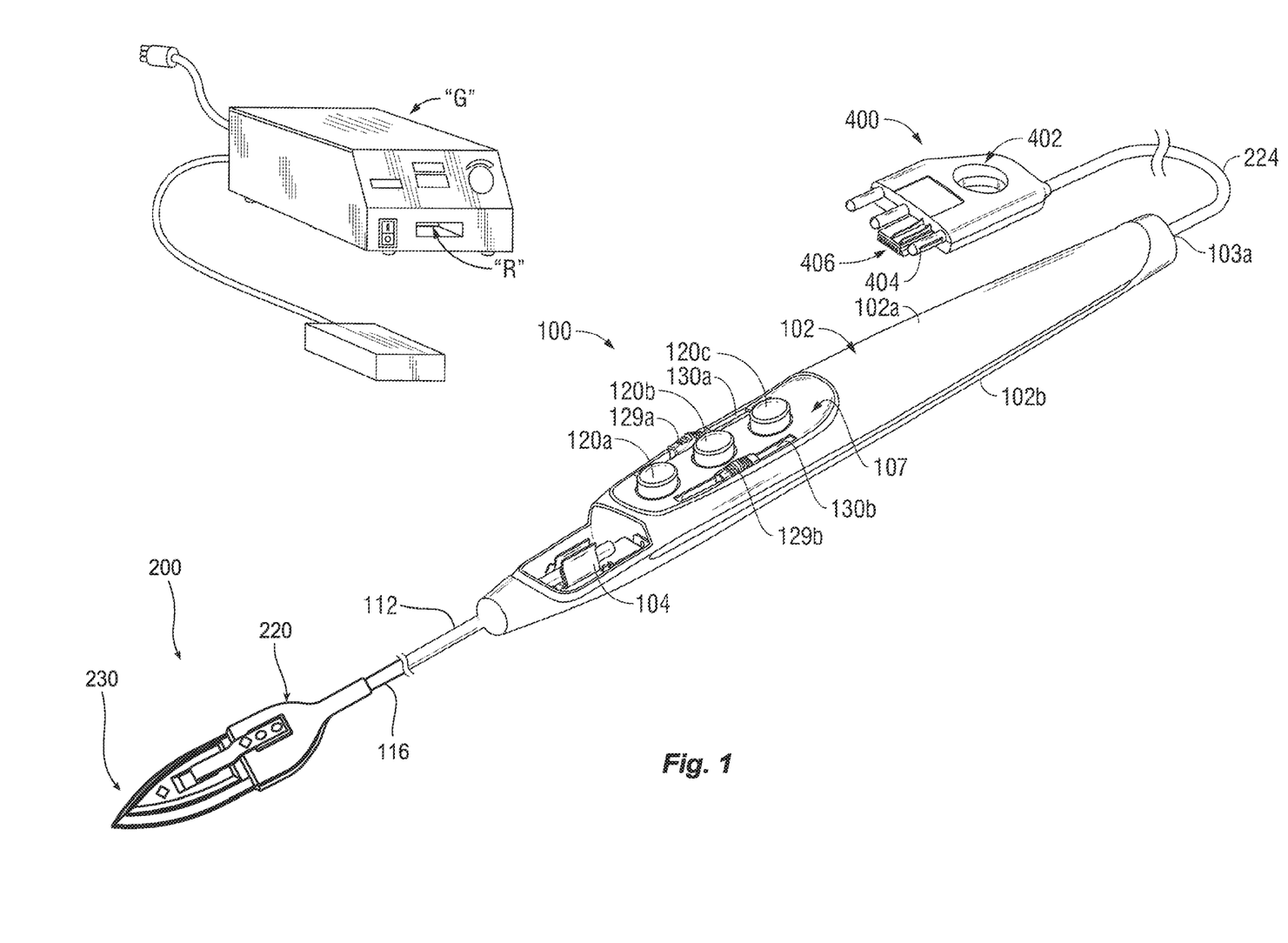
FIG. 1 is a perspective view of an electrosurgical system including an electrosurgical pencil configured for bipolar resection in accordance with an embodiment of the present disclosure.

FIG. 1 sets forth a perspective view of an electrosurgical system including an electrosurgical pencil 100 constructed for bipolar resection in accordance with one embodiment of the present disclosure. While the following description is directed towards electrosurgical pencils for bipolar resection, the features and concepts (or portions thereof) of the present disclosure may be applied to any electrosurgical type instrument, e.g., forceps, suction coagulators, vessel sealers, wands, etc. The construction, functionality and operation of electrosurgical pencils, with respect to use for bipolar resection, is described herein. Further details of the electrosurgical pencil are provided in commonly-owned U.S. Pat. No. 7,156,842 to Sartor et al.

Figure 2:
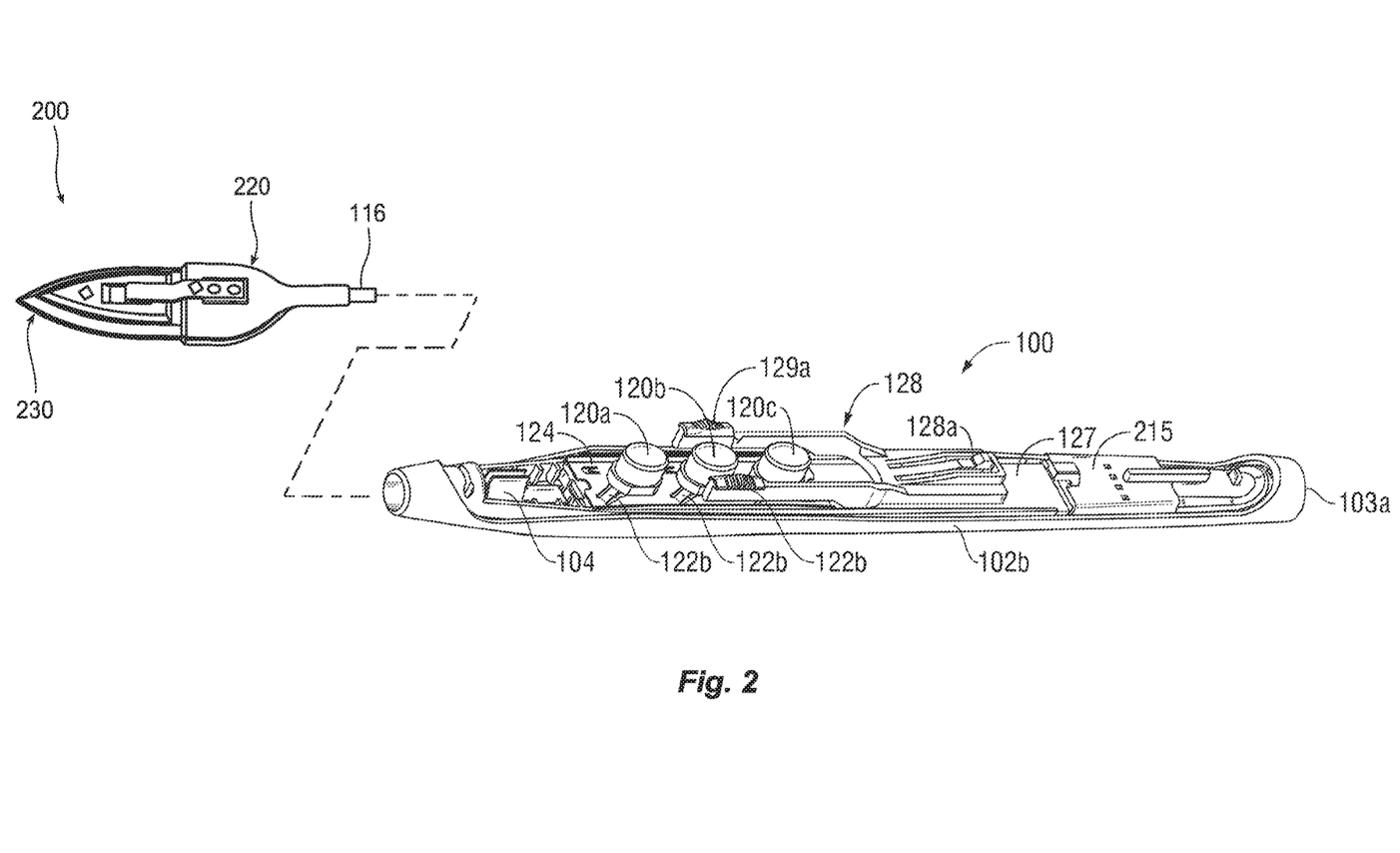
FIG. 2 is a front, top perspective view of the electrosurgical pencil of FIG. 1, with a top-half shell of the housing removed.

As seen in FIGS. 1 and 2, electrosurgical pencil 100 includes an elongated housing 102 having a top-half shell portion 102a and a bottom-half shell portion 102b. The elongated housing 102 includes a distal opening 103b, through which a shaft 112 extends, and a proximal opening 103a, through which connecting wire 224 (see FIG. 1) extends. Top-half shell portion 102a and bottom-half shell portion 102b may be bonded together using any suitable method, e.g., sonic energy, adhesives, snap-fit assemblies, etc.

Electrosurgical pencil 100 further includes a shaft receptacle 104 disposed at a distal end 103b of housing 102 that is configured to receive the haft 112 of a selectively removable end effector assembly 200. Electrode assembly 200 is configured to electrically connect to generator "G" through various electrical conductors formed in the shaft 112, elongated housing 102, connecting wire 224 and plug assembly 400. Generator "G" may be incorporated into the elongated housing 102 and powered by an internal energy supply, e.g., battery or other energy storage device, fuel cell or other energy generation device or any other suitable portable power source.

Shaft 112 is selectively retained by shaft receptacle 104 disposed in housing 102. Shaft 112 may include a plurality of conductive traces or wires along the length of the shaft 112. The conductive traces or wires may be fabricated from a conductive type material, such as, for example, stainless steel, or shaft may be coated with an electrically conductive material. Shaft receptacle 104 is fabricated from electrically conductive materials or includes electrically conductive contacts configured to couple with the plurality of conductive traces or wires of the shaft 112. Shaft receptacle 104 is electrically connected to voltage divider network 127 (FIGS. 2 and 4) as explained in more detail below. Conductive traces or wires of the shaft electrically connect to the electrode assembly as explained in more detail below.

As seen in FIG. 1, electrosurgical pencil 100 may be coupled to a conventional electrosurgical generator "G" via a plug assembly 400 (see FIG. 3), as will be described in greater detail below.

For the purposes herein, the terms "switch" or "switches" includes electrical actuators, mechanical actuators, electromechanical actuators (rotatable actuators, pivotable actuators, toggle-like actuators, buttons, etc.) or optical actuators.

Electrosurgical pencil 100 includes at least one activation switch, and may include three activation switches 120a-120c, each of which extends through top-half shell portion 102a of elongated housing 102. Each activation switch 120a-120c is operatively supported on a respective tactile element 122a-122c provided on a switch plate 124, as illustrated in FIG. 2. Each activation switch 120a-120c controls the transmission of RF electrical energy supplied from generator "G" to bipolar electrodes 138 on electrode face 105 of electrode body 112.

More particularly, switch plate 124 is positioned on top of a voltage divider network 127 (hereinafter "VDN 127") such that tactile elements 122a-122c are operatively associated therewith. VDN 127 (e.g., here shown in FIG. 2 as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage. Further details of electrosurgical pencil control are provided in above-mentioned U.S. Pat. No. 7,503,917 to Sartor et al.

Figure 3:
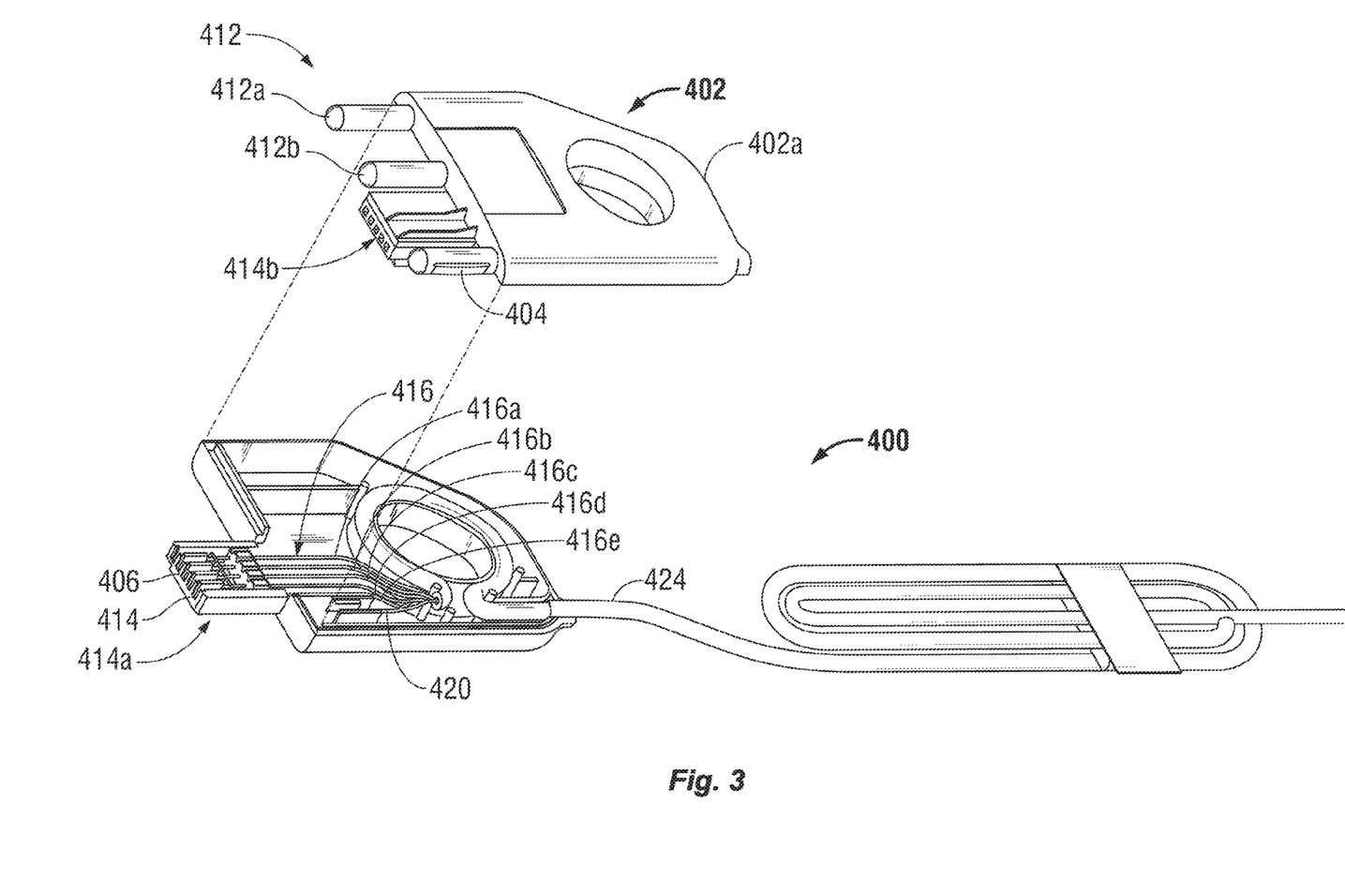
FIG. 3 is a perspective view of the plug assembly of FIG. 1, with a top-half shell section removed therefrom.

In use, depending on which activation switch 120a-120c is depressed a respective tactile element 122a-122c is pressed into contact with VDN 127 and a characteristic signal is transmitted to electrosurgical generator "G" via control wires 416 (see FIG. 3). In one embodiment, three control wires 416a-416c (one for each activation switch 120a-120c, respectively) are provided. Control wires 416a-416c are electrically connected to switches 120a-120c via a control terminal 215 (see FIG. 2) which is operatively connected to VDN 127. By way of example only, electrosurgical generator "G" may be used in conjunction with the device wherein generator "G" includes a circuit for interpreting and responding to the VDN 127 settings.

Activation switches 120a, 120b, 120c are configured and adapted to control the mode and/or "waveform duty cycle" to achieve a desired surgical intent. For example, a first activation switch 120a can be set to deliver a characteristic signal to electrosurgical generator "G" which, in turn, transmits a duty cycle and/or waveform shape that produces a first desirable resection effect. Meanwhile, second activation switch 120b can be set to deliver a characteristic signal to electrosurgical generator "G" which, in turn, transmits a duty cycle and/or waveform shape that produces a second desirable resection effect.

Finally, third activation switch 120c can be set to deliver a characteristic signal to electrosurgical generator "G" which, in turn, transmits a duty cycle and/or waveform shape that produces a third electrosurgical effect/function. Desirable resection effects may include a mode for bipolar coagulation and/or cauterization with an undeployed blade, a mode for bipolar resection with a partially deployed blade, a mode for bipolar resection with a fully deployed blade, a mode for monopolar resection and a mode for resection with blended energy delivery (monopolar and bipolar modes), as will be described in greater detail hereinbelow.

Figures 6A, 6B:
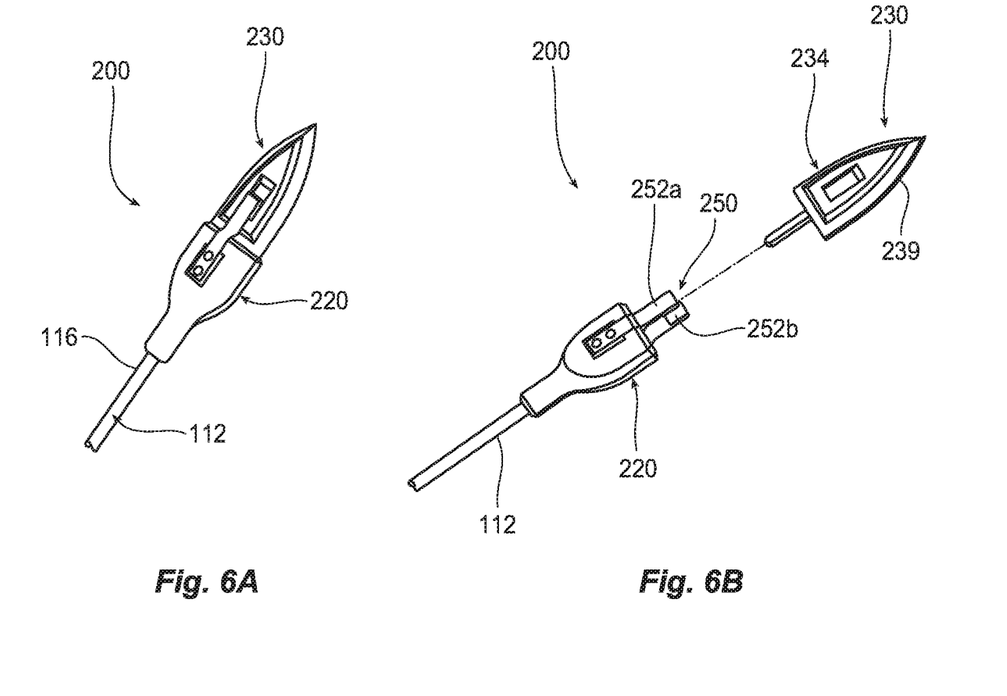
FIG. 6A is an enlarged, top, perspective view of the end effector assembly of the present disclosure.
FIG. 6B is an enlarged, top, perspective view of the end effector assembly of FIG. 6A showing a removable distal tip separated from an end effector housing.

As seen in FIG. 3, fourth and fifth wires (e.g., first RF line 416d and second RF line 416e) are provided and electrically connect to respective active and return electrodes 239, 234 of the end effector assembly 200 (See FIG. 6B). Since first RF line 416d and second RF line 416e are directly connected to the end effector assembly 200, first RF line 416d and second RF line 416e bypass the VDN 127 and are isolated from VDN 127 and control wires 416a-416c. By directly connecting the first RF line 416d and second RF line 416e to the end effector assembly 200 (as explained in more detail below) and isolating the VDN 127 from the RF energy transmission, the electrosurgical current does not flow through VDN 127. This in turn, increases the longevity and life of VDN 127 and/or activation switches 120a, 120b, 120c.

Figure 4:
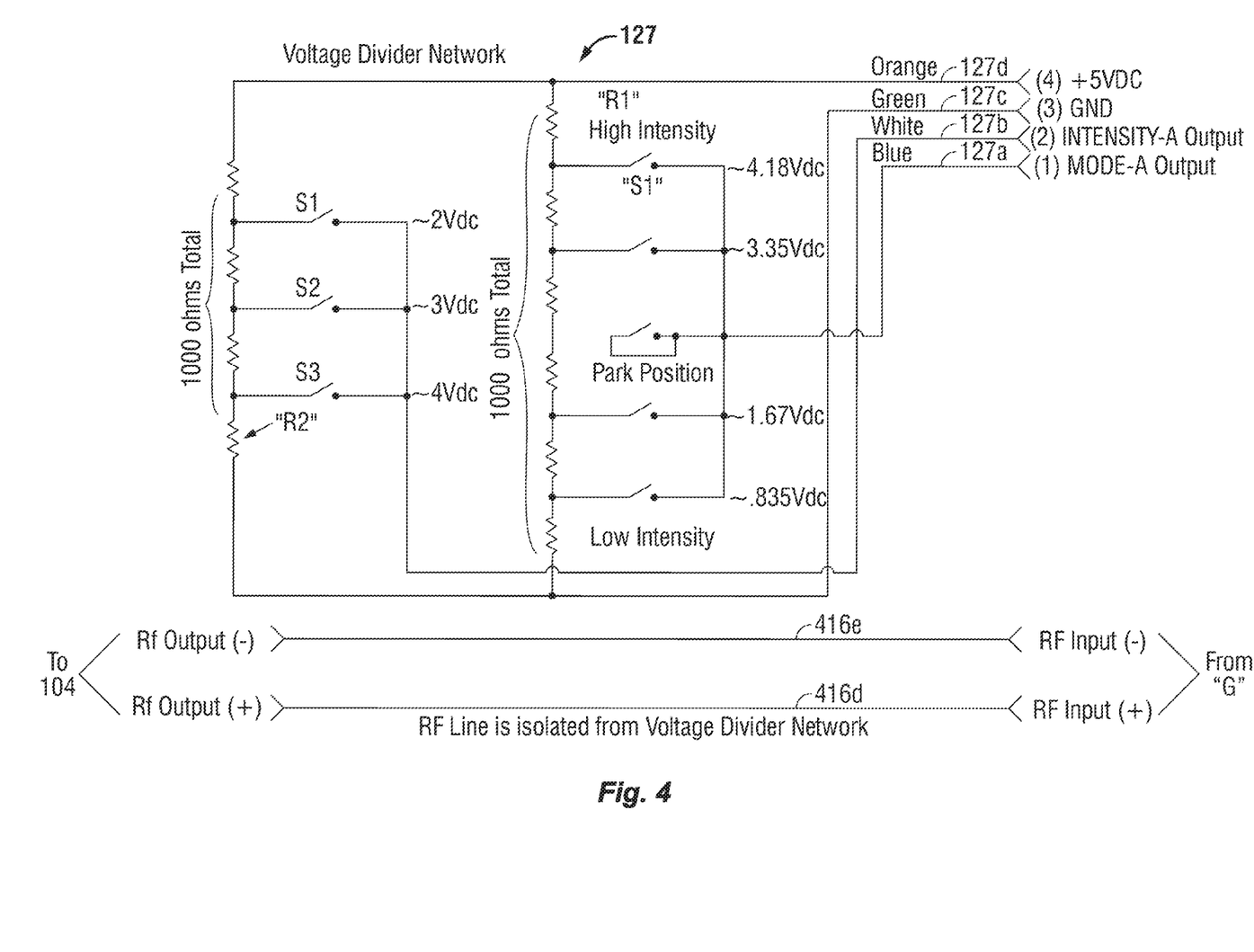
FIG. 4 is a schematic illustration of the voltage divider network of the present disclosure.

With reference to FIG. 4, VDN 127 is shown and includes a first transmission line 127a configured to operate the various modes of electrosurgical pencil 100; a second transmission line 127b configured to operate the various intensities of electrosurgical pencil 100; a third transmission line 127c configured to function as a ground for VDN 127; and a fourth transmission line 127d which transmits up to about +5 volts to VDN 127.

First RF line 416d and second RF line 416e are isolated from or otherwise completely separate from VDN 127. In particular, first RF line 416d and second RF line 416e extends directly from the RF input or generator "G" to the active electrode 239 and return electrodes 234a, 234b of the end effector assembly 200 as explained in more detail below.

By way of example only, VDN 127 may include a plurality of resistors "R1" (e.g., six resistors), connected in a first series between third transmission line 127c and fourth transmission line 127d. The first series of resistors "R1" may combine to total about 1000 ohms of resistance. The first series of resistors "R1" are each separated by a first set of switches "S1". Each switch of the first set of switches "S1" may be electrically connected between adjacent resistors "R1" and first transmission line 127a of VDN 127. In operation, depending on which switch or switches of the first set of switches "S1" is/are closed, a different mode of operation for electrosurgical pencil 100 is activated.

Resection may be performed with electrosurgical energy including waveforms having a duty cycle from about 10% to about 100%. The dual effect of coagulating and cauterizing, as described herein, may be performed with a waveform having a duty cycle from about 10% to about 100%. To increase the depth of coagulation may require a waveform with a duty cycle from about 50% to 100%. It is important to note that these percentages are approximated and may be customized to deliver the desired surgical effect for various tissue types and characteristics.

In one embodiment, the waveforms provided to the bipolar electrosurgical pencil 100 may be dynamically controlled by the generator "G". For example, the mode of operation provided by switches S1, S2, S3 may indicate a range of operation for the generator "G". Generator "G" provides a waveform within the specified range of operation wherein the waveform is dynamically changed based on a parameter, wherein the parameter may be related to one of energy delivery, the target tissue and the duration of energy delivery. The parameter may be obtained from a source external to the generator "G", such as, a measured parameter or clinician provided parameter, or the parameter may include an internal parameter obtained, measured or determined by the generator "G".

As seen throughout FIG. 2, electrosurgical pencil 100 further includes an intensity controller 128 slidingly supported on or in elongated housing 102. Intensity controller 128 may be configured to function as a slide potentiometer, sliding over and along VDN 127 wherein the distal-most position corresponds to a relative high intensity setting, the proximal-most position corresponds to a low intensity settings with a plurality of intermediate positions therebetween. As can be appreciated, the intensity settings from the proximal end to the distal end may be reversed, e.g., high to low.

The intensity settings are typically preset and selected from a look-up table based on a choice of electrosurgical instruments/attachments, desired surgical effect, surgical specialty and/or surgeon preference, the type of end effector assembly 200 and the arrangement of the active and return electrodes 239, 234a, 234b. The selection of the end effector assembly 200, the intensity setting and duty cycle determines the surgical effect. The settings may be selected manually by the user or automatically. For example, the electrosurgical generator "G" may automatically determine the type of end effector assembly 200 and a predetermined intensity value may be selected and subsequently adjusted by the user or the electrosurgical generator "G".

Turning now to FIG. 3, a detailed discussion of plug assembly 400 is provided. Plug assembly 400 includes a housing portion 402 and a connecting wire 424 that electrically interconnects the housing portion 402 and the control terminal 215 in the electrosurgical pencil 100 (see FIG. 2). Housing portion 402 includes a first half-section 402a and a second half-section 402b operatively engageable with one another, e.g., via a snap-fit engagement. First half-section 402a and second half-section 402b are configured and adapted to retain a common power pin 404 and a plurality of electrical contacts 406 therebetween.

Common power pin 404 of plug assembly 400 extends distally from housing portion 402 at a location between first half-section 402a and second half-section 402b. Common power pin 404 may be positioned to be off center, i.e., closer to one side edge of housing portion 402 than the other. Plug assembly 400 further includes at least one pair of position pins 412 also extending from housing portion 402. Position pins 412 may be positioned between the first half-section 402a and the second half-section 402b of housing portion 402 and are oriented in the same direction as common power pin 404.

A first position pin 412a is positioned in close proximity to a center of housing portion 402 and a second position pin 412b is positioned to be off center and in close proximity to an opposite side edge of housing portion 402 as compared to common power pin 404. First position pin 412a, second position pin 412b and common power pin 404 may be located on housing portion 402 at locations which correspond to pin receiving positions (not shown) of a connector receptacle "R" of electrosurgical generator "G" (see FIG. 1).

Plug assembly 400 further includes a prong 414 extending from housing portion 402. In particular, prong 414 includes a body portion 414a extending from second half-section 402b of housing portion 402 and a cover portion 414b extending from first half-section 402a of housing portion 402. In this manner, when the first half-section 402a and the second half-section 402b are joined to one another, cover portion 414b of prong 414 encloses the body portion 414a. Prong 414 may be positioned between common power pin 404 and first position pin 412a. Prong 414 is configured and adapted to retain electrical contacts 406 therein such that a portion of each electrical contact 406 is exposed along a front or distal edge thereof. While five electrical contacts 406 are shown, any number of electrical contacts 406 can be provided, including and not limited to two, six and eight. Prong 414 may be located on housing portion 402 at a location that corresponds to a prong receiving position (not shown) of connector receptacle "R" of electrosurgical generator "G" (see FIG. 1).

Since prong 414 extends from second half-section 402b of housing portion 402, housing portion 402 of plug assembly 400 will not enter connector receptacle "R" of electrosurgical generator "G" unless housing portion 402 is in a proper orientation. In other words, prong 414 functions as a polarization member. This ensures that common power pin 404 is properly received in connector receptacle "R" of electrosurgical generator "G".

Connecting wire 424 includes a power supplying wire 420 electrically connected to common power pin 404, control wires 416a-416c electrically connected to a respective electrical contact 406, and first RF line 416d and second RF line 416e electrically connected to a respective electrical contact 406.

Figure 5:
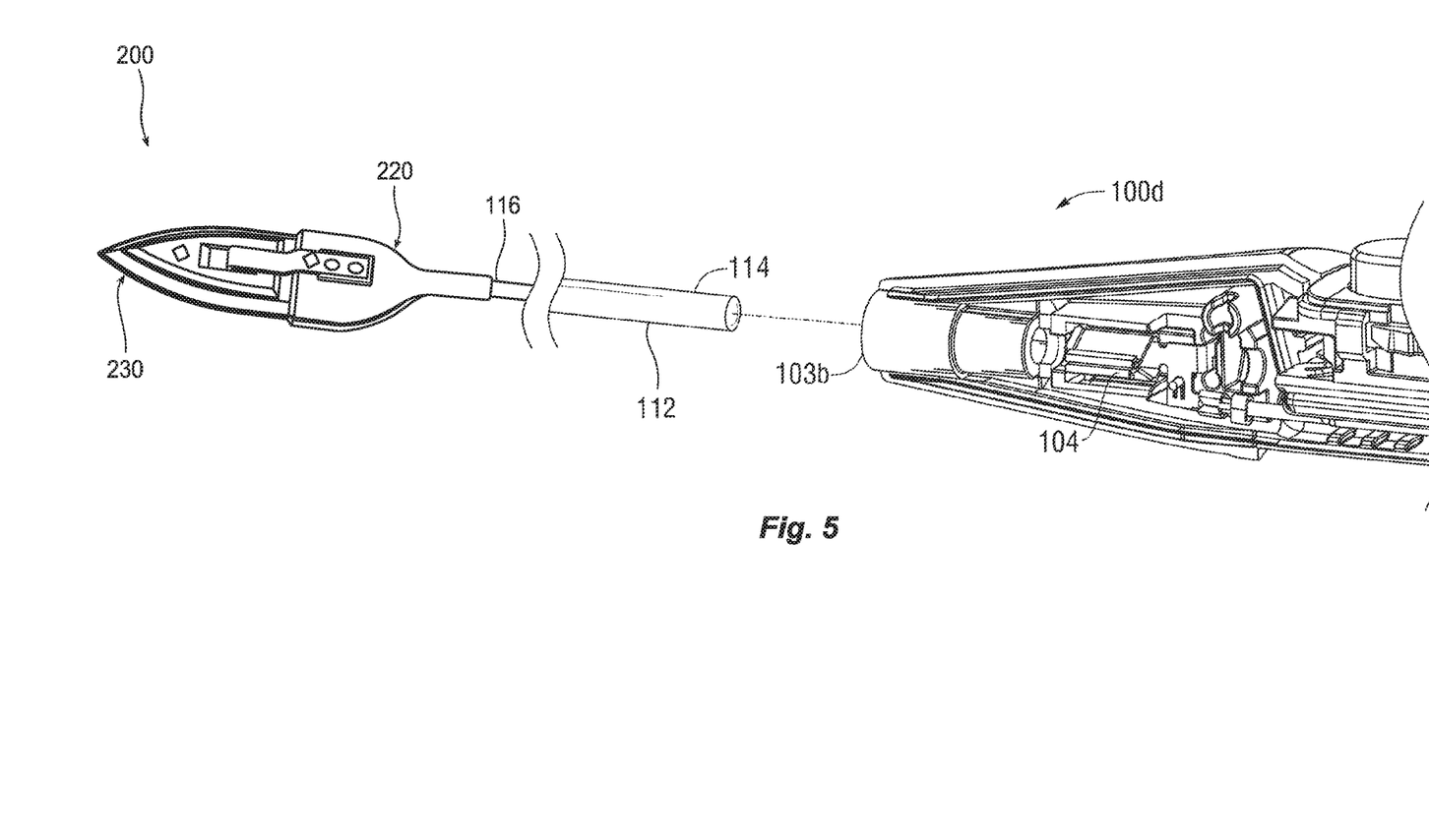
FIG. 5 is a partial, cross-sectional view of an end effector assembly of an electrosurgical pencil, in accordance an embodiment of the present disclosure.
Figure 6C:
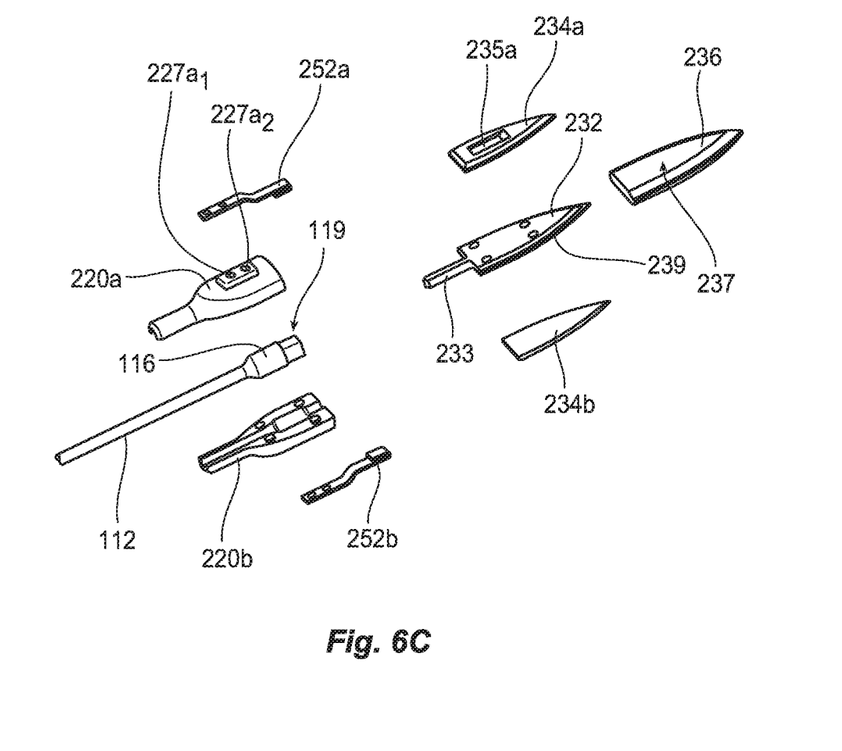
FIG. 6C is an enlarged, exploded view of the end effector assembly of FIG. 6A.
Figure 7:
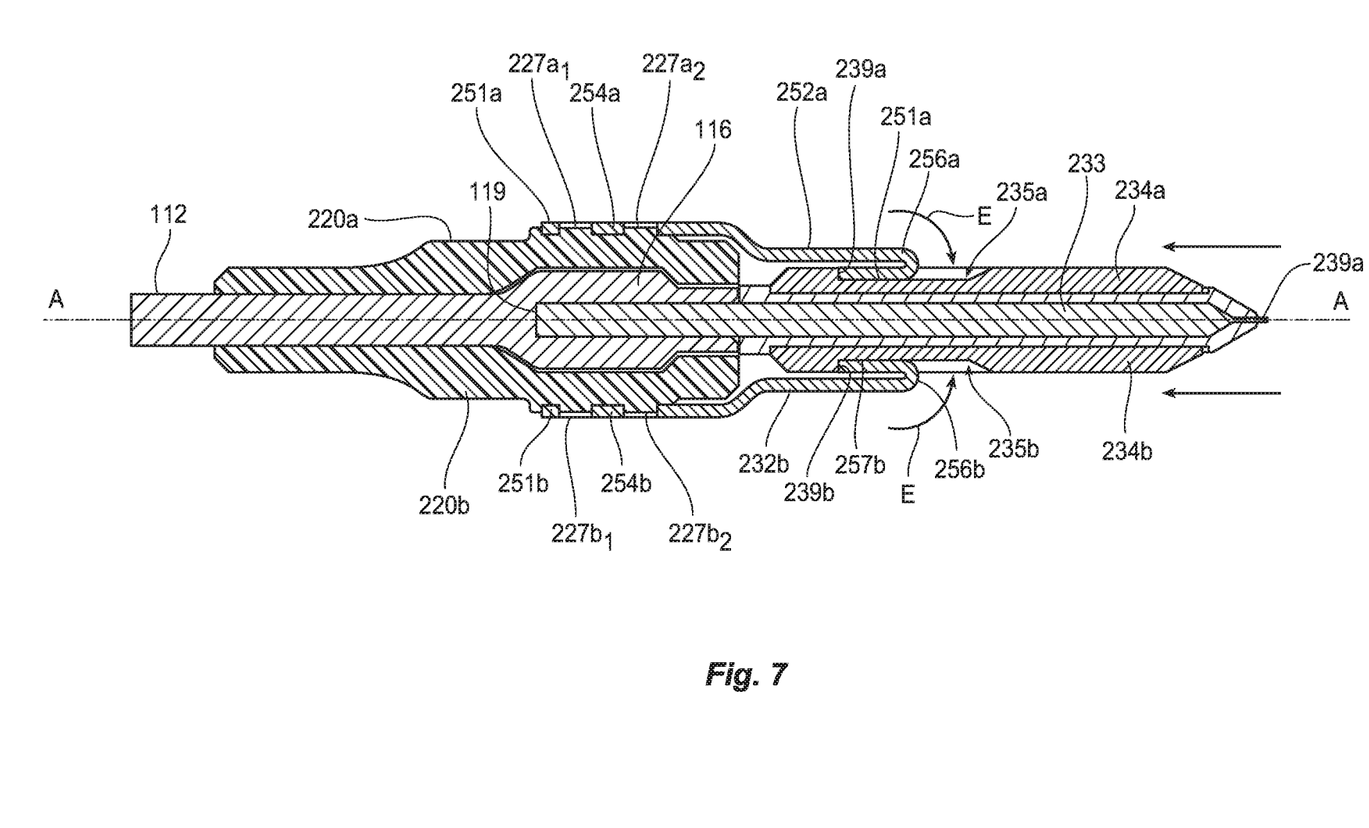
FIG. 7 is a side, cross sectional view of the end effector assembly illustrating engagement of the removable distal tip with the end effector housing.

Turning now to FIG. 5, the end effector assembly 200 of electrosurgical pencil 100 is shown wherein a proximal portion 114 of shaft 112 is configured to mechanically and electrically engage shaft receptacle 104. Shaft 112 and shaft receptacle 104 are configured to provide a plurality of suitable electrical connections therebetween to facility the delivery of electrosurgical energy from the electrosurgical generator "G" (See FIG. 1) to the active and two return electrodes 239 and 234a, 234b of the end effector assembly 200 as explained in further detail with respect to FIG. 6C.

At least a portion of the shaft 112 is inserted into distal opening 103b of the elongated housing 102 to engage shaft receptacle 104. Shaft receptacle 104 is configured to mechanically and electrically couple the shaft 112 to the elongated housing 102. Electrical connections may include one or more electrical connectors (or electrical connector pairs) that connect to the active and return electrodes 23p, 234a and 234b. Shaft 112 and shaft receptacle 104 may include a locking device, such as, for example, a shaft locking pin that slides into and engages a shaft locking pin receptacle (not explicitly shown). Any suitable securing and/or locking apparatus may be used to releasably secure the shaft 112 to the elongated housing 102. As described herein, the shaft 112 is interchangeable with the elongated housing 102. In other embodiments, shaft 112 is integrated into the elongated housing 102 and is not replaceable.

FIGS. 6A-8 show various views of one embodiment of the end effector assembly 200 for use with the electrosurgical pencil 100. End effector assembly 200 includes a housing 220 that is configured to mechanical and electrically couple to a distal end 116 of shaft 112. Housing includes two housing halves 220a and 220b that cooperate to encase the distal end 116 of shaft 112. The housing halves 220a, 220b may be ultrasonically welded together or mechanically engaged in some other fashion, e.g., snap-fit, adhesive, etc. The distal end 116 of shaft 112 includes a collet 119 that is configured to mechanical engage a proximal end 233 of the active electrode 239 (See FIG. 7). An insulator 236 engages the active electrode 239 in a generally slip-fit manner allowing the edge 239 thereof to protrude through the sides and tip of the insulator 236 (See FIG. 7). The active electrode 239 may be arrow-shaped to include a tip 239a at the distal end thereof. The exposed edge 239 may be sharpened to facilitate mechanical cutting.

Figure 8:
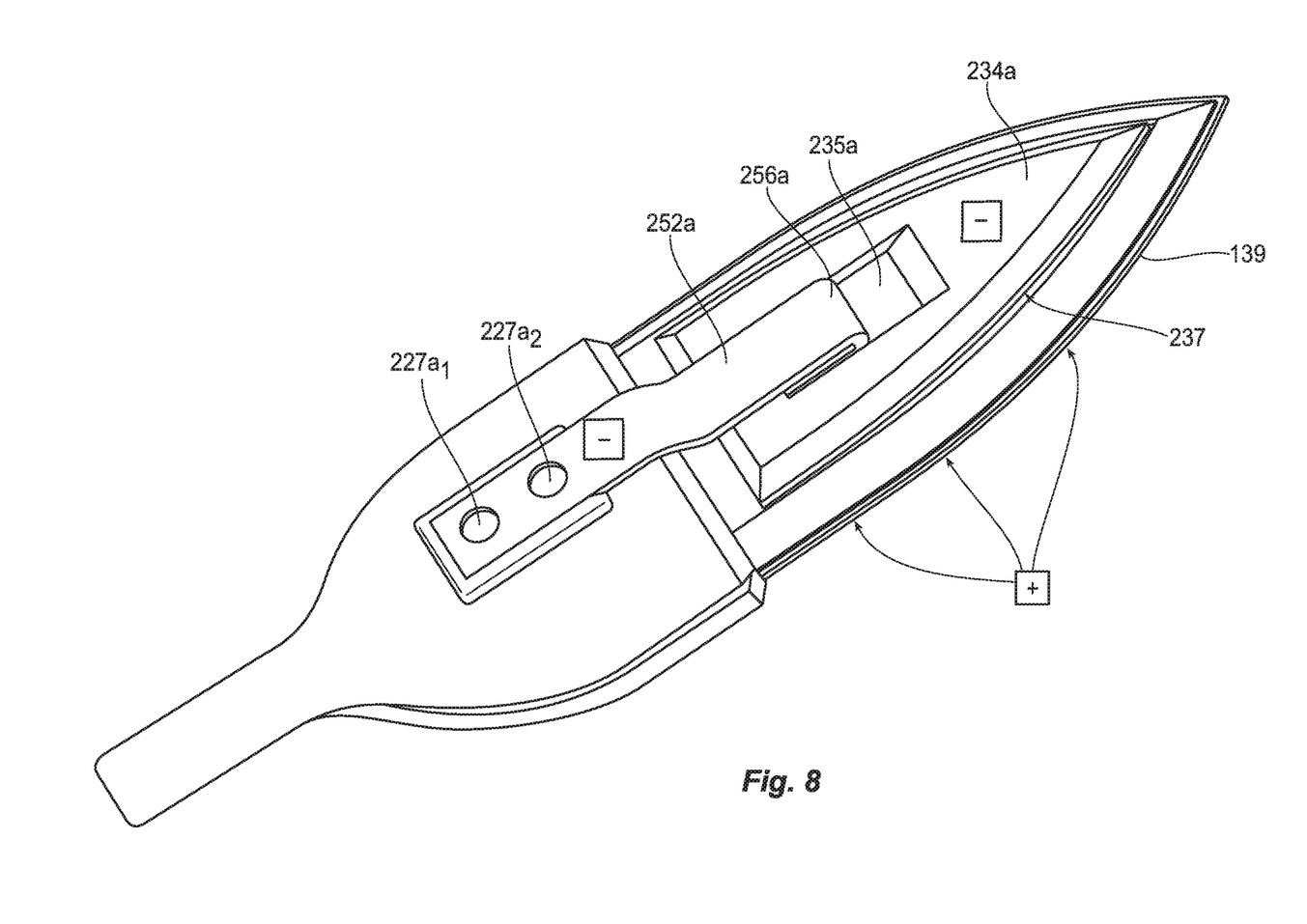
FIG. 8 is an enlarged, top perspective view of the end effector assembly highlighting a cutting edge of the removable distal tip.

The return electrodes 234a, 234b are configured to engage the outer peripheral surface of the insulator 236 and rest inside a corresponding recess 237 defined therein on either side thereof (See FIG. 8). Each return electrode 234a, 234b includes a corresponding recess 235a, 235b defined therein configured to receive a distal end 256a, 256b of a respective spring clip 252a, 252b. The proximal end of each spring clip 252a, 252b includes a plurality of respective mechanical interfaces 251a, 254a and 251b, 254b that mechanically engage a respective housing half 220a, 220b. Each housing half 220a, 220b includes a respective pair of detents 227a1, 227a2 and 227b1, 227b2 that provide additional mechanical engagement of the respective spring clips 252a, 252b atop the housing halves 220a, 220b.

Once all components are assembled on shaft 112, namely, housing 220, active electrode 239, return electrodes 234a, 234b, and insulator 236, the bias of the opposing spring clips 252a, 252b engage and lock the active and return electrodes 239 and 234a, 234b in place atop the housing 220. More particularly, the distal end 256a, 256b of each spring clip 252a, 252b is generally C-shaped to include a trailing leg 257a, 257b. Upon engagement of the active electrode 239, return electrodes 239a, 239b and insulator 236 with the housing 220, each trailing leg 257a, 257b rotates in the direction of arrow "E" to snap and seat within respective recesses 235a, 235b of return electrode 234a, 234b and abuts against a respective proximal lip 239a, 239b of each recess 235a, 235b to lock the spring clips 252a, 252b within the recesses 235a, 235b which, in turn, locks the electrodes 239 and 234a, 234b atop the insulator 236. The abutment of trailing legs 239a, 239b with the proximal lips 239a, 239b of recesses 235a, 235b prevents removal of the return electrodes 234a, 234b along the longitudinal axis A-A without initially disengaging the clips 252a, 252b (e.g., prying the clips away from the longitudinal axis A-A in a direction opposite arrows "E").

In addition and upon engagement of the spring clips 252a, 252b atop the electrodes 239 and 234a, 234b, the rotational bias of the spring clips 252a, 252b (in the direction of arrows "E") as well as the abutment of the trailing legs 257a, 257b with proximal lips 239a, 239c lock the proximal end 233 of the active electrode within the collet 119.

The active electrode 239 may be made from any suitable conductive material such as tungsten, surgical stainless steel, etc. Tungsten is particularly favored since various geometries for the active electrode 239 may be easily 3D printed providing additional robustness over traditional wire designs while offering an optimized surface area to increase cutting efficiency. Moreover a sheet including a plurality of tungsten active electrodes 239 may be 3D printed to facilitate the manufacturing process. Moreover, multiple geometries may be easily integrated with the mating geometry of the various mechanical interfaces staying the same.

The leading edge 239a of the active electrode 239 is configured for cutting and is designed to concentrate electrosurgical energy to increase cutting efficiency. The active electrode 239 is electrically connected via the shaft 112 (or an internal element thereof—not shown). The return electrodes 234a, 234b are made from a conductive material and insulated from the active electrode 239 via the insulator 236. The insulator 236 may be made from Alumina ceramic, or some other material that provides good thermal and non-conductive properties. Each return electrode 234a, 234b provides a return path for the electrosurgical energy from the active electrode 239 such that the circuit is completed.

As mentioned above, the spring clips 252a, 252b retain the active and return electrodes 239 and 234a, 234b atop the housing 220 and also provide a secondary function of providing the bridge between the ground electrodes 234a, 234b and the ground return wiring (not shown). In embodiments, insulated wiring (not shown) may be incorporated through shaft 112 and terminate on or around detents 227a1, 227a2 and 227b1, 227b2 which, in turn, are configured to provide electrical continuity to mechanical interfaces 251a, 254a and 251b, 254b of spring clips 252a, 252b. When assembled, the various electrical connections are made and may be spliced to one or more wires configured to travel back through pen housing 102 to plug 400 for ultimate connection to the generator "G". This completes circuit to allow bipolar cutting to occur.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. For example, the knife body and tube do not necessarily have to be made from the exact same materials. Similar materials, or any two materials that can be welded together to allow for a durable weld joint could be used.

The invention claimed is:

1. An electrode assembly for an electrosurgical instrument, comprising:
   a housing configured to operably receive a distal end of an electrosurgical instrument shaft, the housing including a pair of opposing spring clips on either side thereof;
   an active electrode including a proximal end configured to selectively engage the housing and the distal end of the shaft, the active electrode including a cutting edge defined about a periphery thereof;
   an insulator configured to encapsulate the active electrode while leaving the cutting edge exposed; and
   a pair of return electrodes each configured to operably engage an exposed side of the insulator on opposing sides thereof, each return electrode including a recess defined therein configured to removably receive a distal end of each respective spring clip of the housing such that, upon selective engagement of the active electrode with the distal end of the shaft, each spring clip removably snaps into each respective recess to removably lock the active and return electrodes to the housing.

2. The electrode assembly of claim 1 wherein the insulator is at least one of an electrical or thermal insulator.

3. The electrode assembly of claim 1 wherein the active electrode includes tungsten.

4. The electrode assembly of claim 1 wherein the cutting edge of the active electrode is sharp to facilitate mechanical cutting of tissue.

5. The electrode assembly of claim 1 wherein the housing includes at least one detent configured to engage a corresponding at least one aperture defined within at least one of the spring clips.

6. The electrode assembly of claim 1 wherein the housing includes two opposing housing halves configured to encapsulate the distal end of the shaft.

7. The electrode assembly of claim 1 wherein a proximal end of the active electrode is configured to mechanically engage a collet defined within the distal end of the shaft.

8. The electrode assembly of claim 1 wherein each spring clip includes a C-shaped distal end configured to abuttingly engage a proximal lip of each corresponding recess of each return electrode to removably retain each return electrode with the housing.

9. The electrode assembly of claim 1 wherein the active electrode is generally arrow-shaped and includes a tip at an end thereof.

10. The electrode assembly of claim 1, wherein the spring clips are attached to the housing when the housing is free from engagement with the distal end of the electrosurgical instrument shaft.

11. The electrode assembly of claim 1, wherein each return electrode of the pair of return electrodes is configured to selectively engage the housing.

12. An electrode assembly for an electrosurgical instrument, comprising:
    a housing configured to operably receive a distal end of an electrosurgical instrument shaft, the housing including a pair of opposing housing halves configured to encapsulate the distal end of the shaft;
    a pair of opposing spring clips attached to respective housing halves;
    an active electrode including a proximal end configured to selectively engage the distal end of the shaft, the active electrode including a cutting edge defined about a periphery thereof;
    an insulator configured to encapsulate the active electrode while leaving the cutting edge exposed; and
    a pair of return electrodes each configured to operably engage an exposed side of the insulator on opposing sides thereof, each return electrode including a recess defined therein configured to removably receive a distal end of each respective spring clip of each housing half such that, upon selective engagement of the active electrode with the distal end of the shaft, a distal end of each spring clip removably snaps into each respective recess to removably lock the active and return electrodes to the housing.

13. The electrode assembly of claim 12 wherein the insulator is at least one of an electrical or thermal insulator.

14. The electrode assembly of claim 12 wherein the active electrode includes tungsten.

15. The electrode assembly of claim 12 wherein the cutting edge of the active electrode is sharp to facilitate mechanical cutting of tissue.

16. The electrode assembly of claim 12 wherein the housing includes at least one detent configured to engage a corresponding at least one aperture defined within at least one of the spring clips.

17. The electrode assembly of claim 12 wherein a proximal end of the active electrode is configured to mechanically engage a collet defined within the distal end of the shaft.

18. The electrode assembly of claim 12 wherein each spring clip includes a C-shaped distal end configured to abuttingly engage a proximal lip of each corresponding recess of each return electrode to removably retain each return electrode with the housing.

19. The electrode assembly of claim 12 wherein the active electrode is generally arrow-shaped and includes a tip at an end thereof.

20. The electrode assembly of claim 12, wherein the active electrode and each return electrode of the pair of return electrodes are configured to selectively engage the housing.

* * * * *